United States Patent [19]

Powell et al.

[11] 4,153,616

[45] May 8, 1979

[54] PROCESS FOR THE PREPARATION OF ALKENYLATED DICARBOXYLIC ACID LACTONES

[75] Inventors: Justin C. Powell, Wappingers Falls; William M. Cummings, Fishkill, both of N.Y.

[73] Assignee: Texaco Inc., New York, N.Y.

[21] Appl. No.: 735,871

[22] Filed: Oct. 26, 1976

[51] Int. Cl.² ............... C07D 309/30; C07D 307/32
[52] U.S. Cl. ............................ 260/343.5; 260/343.6
[58] Field of Search ........................... 260/343.5, 343.6

[56] References Cited

U.S. PATENT DOCUMENTS

| | | | |
|---|---|---|---|
| 3,155,685 | 11/1964 | Prill et al. | 260/343.5 |
| 3,155,686 | 11/1964 | Prill et al. | 260/343.6 |
| 3,248,187 | 4/1966 | Bell | 44/63 |
| 3,267,062 | 8/1966 | Prill et al. | 260/30.4 |

Primary Examiner—Norma S. Milestone
Attorney, Agent, or Firm—Thomas H. Whaley; Carl G. Ries; James J. O'Loughlin

[57] ABSTRACT

An improvement in a process for the preparation of alkenyldicarboxylic acid lactones by alkenylation of maleic anhydride or other $C_4H_2O_3$, $C_5H_4O_3$, or $C_6H_6O_3$ alkendioic anhydrides or their corresponding acids wherein the unsaturation is conjugated with at least one carboxy group with olefins having a molecular weight from about 200 to 3000 whereby alkenyldicarboxylic acids or its anhydrides is formed together with a sludge and is thereafter subjected to lactonization or hydrolysis-lactonization in the presence of a catalyst and in the presence of at least a portion of the sludge.

5 Claims, No Drawings

PROCESS FOR THE PREPARATION OF ALKENYLATED DICARBOXYLIC ACID LACTONES

BACKGROUND OF THE INVENTION

1. Field of the Invention

This invention relates to a process for the preparation of alkenyl dicarboxylic acid lactones by alkenylation of a dicarboxylic acid or its anhydride whereby an alkenyl dicarboxylic acid anhydride is formed together with a sludge and the resultant alkenyl dicarboxylic acid anhydride is subjected to hydrolysislactonization in the presence of said sludge and a catalyst.

2. Discussion of the Prior Art

The preparation of alkenyl dicarboxylic acid lactones is known. Such lactones include alkenyl succinic acid lactone, which is useful as a dispersant in a motor fuel composition or as an intermediate for the preparation of motor fuel and lubricant additives. These alkenyl dicarboxylic acid lactones are particularly useful as gasoline additives to provide a detergent action to an automotive carburetor and to inhibit corrosion in the lines through which the gasoline passes. They are also useful in lubricant compositions or dispersants.

Alkenyl dicarboxylic acid lactones have been heretofore prepared in a multi-step, multi-pot process. In the first step, the dicarboxylic acid reactant, usually in the form of the anhydride, is charged to a reactor into which is introduced the alkenylating agent, typically a low molecular weight polyolefin having a molecular weight in the range of 200–3000. The reaction mixture is stirred while heat is applied to the same. Conventionally, alkenylation is performed at elevated temperatures of up to 300° C. As a result of the alkenylation, the alkenylated anhydride is formed together with a sludge, believed to be a decomposition product of the unsaturated dicarboxylic acid or anhydride reactant.

Lactonization was not effected until the intermediate anhydride was isolated from the unreacted dicarboxylic acid/anhydride and sludge. Generally, this was done by first stripping the unreacted acid/anhydride and thereafter pumping the intermediate sludge mixture over a filter to filter out the sludge and isolate a mixture of the alkenyl dicarboxylic anhydride intermediate in unreacted polyolefin for subsequent lactonization of the anhydride.

The mixture was thereafter charged to still another reactor for lactonization into which was introduced the required agents for hydrolysis-lactonization, usually a minor quantity of water and a catalyst. Lactonization was effected by heating the reaction mixture at an elevated temperature up to 100° C. As catalyst, a protonating or electrophilic catalyst including sulfuric acid, boron trifluoride, perchloric acid and sulfonic acid macroreticular ion exchange resins was used. Lactonization was effected with stirring until the desired product was obtained. The reaction product was thereafter pumped over a second filter to filter out solid material and the liquid was passed into a storage tank. Before use, the liquid lactone produce could be treated with a neutralizing agent such as diethylene triamine to neutralize residual acid values in the product.

It was discovered that notwithstanding the multiple steps required for such alkenyl dicarboxylic acid lactones, that a substantial amount of neutralizing agent was required owing to the presence of substantial quantities of residual acid catalyst in the resultant product. It therefore became desirable to provide a process for the preparation of alkenyl dicarboxylic acid lactones wherein the resultant lactone product could be obtained according to a simplified process. Moreover, it became desirable to provide such a simplified process whereby the resultant lactone product contained substantially less residual acid catalyst.

SUMMARY OF THE INVENTION

The objects of this invention are realized in a process for the preparation of an alkenyl dicarboxylic acid lactone by alkenylation of a dicarboxylic acid such as maleic acid, itaconic acid, or other $C_4$ to $C_6$ alkendioic acid wherein the unsaturated is conjugated with at least one carboxy group or its corresponding anhydride, whereby an alkenyl dicarboxylic acid anhydride is formed together with sludge and the resultant alkenyl dicarboxylic acid anhydride is subjected to lactonization, the process being carried out according to the invention in the presence of at least a portion of said sludge.

It has been discovered that alkenyl dicarboxylic acid lactones can be provided in an essentially two-step, one-pot process in which, in a first step, a dicarboxylic acid set forth above or its corresponding anhydride can be alkenylated, such as by use of an olefin. The resultant alkenyl dicarboxylic acid anhydride can be subjected to lactonization in the presence of the sludge which forms therewith. It has been surprisingly discovered that, instead of the sludge impairing the lactonization process, in fact, the resultant lactonization product is purer following the usual extraction of water soluble materials than is the product obtained by lactonization performed only after all sludge is separated from the alkenyl dicarboxylic acid anhydride intermediate.

According to the process of the invention, an alkenyl dicarboxylic acid or its corresponding anhydride is first subjected to alkenylation. Usually this is performed by contacting the alkendoic acid or anhydride with an olefin having a molecular weight, determined in accordance with vapor pressure osmometry, of about 200 to 3000. Preferably the polyolefin will have a molecular weight in the range of about 200–1400 if the product is intended for use in gasoline and a molecular weight in the ragne of about 200–3000 if it is intended for use in a lubricating oil. These olefins can be derived from monomers of $C_2$ to $C_6$. Direct thermal alkenylation of dicarboxylic acids or anhydrides can be performed with olefins of $C_{12}$ and higher.

Alkenylation is effected at a temperature between the melting point of the acid or anhydride (52° C. in the case of maleic acid anhydride) and 300° C., preferably 180° C. to 250° C. and more preferably 200° C. to 240° C. employing a mole ratio of dicarboxylic acid/anhydride to olefin of 1:5 to 5:1, preferably 1:2 to 3:1. An especially contemplated acid/anhydride : olefin mole ratio is 0.75:1 to 2.5:1.0. Alkenylation is preferably effected by agitating the reaction mixture and passing thereover a blanket of an inert gas such as nitrogen, carbon dioxide or the like in order to purge the system of air. The alkenylation is effected for a period of time between 0.5 and 50 hours, preferably 5 to 25 hours and especially 8 to 14 hours. A wide range of pressure from 0.8 atmospheres up to 100 atmospheres can be employed. It is especially contemplated to carry out the process at ambient temperature or in an autoclave under autogenous pressure. To facilitate the reaction, catalysts, inhibitors, surfactants, or solvents can be used.

Radiant or ultrasonic energy can be employed to assist the reaction.

As a result of the alkenylation, there is formed the aforementioned sludge. This sludge is in the form of a dark solid granular mass and is believed to be a decomposition product of the dicarboxylic acid/anhydride. The lactonization is effected in the presence of at least a portion of this sludge. Preferably, prior to lactonization, excess or unreacted dicarboxylic acid/anhydride is removed from the alkenylation reaction product. This can be done by reducing the pressure on the reaction product to within the range of about 10 to 50 mm Hg, especially about 20 to 50 mm Hg, while adjusting the temperature of the reaction mixture to about 200° to 250° C. Under such conditions, the unreacted dicarboxylic acid/anhydride can readily be removed by vacuum distillation from the reaction product.

To the reaction product, preferably free of unreacted unsaturated dicarboxylic acid/anhydride, there is introduced a quantity of water to allow for hydrolysis of the alkenyl dicarboxylic acid anhydride prepared from the alkenylation. Preferably, the lactonization is effected in the presence of only a minor quantity of water, namely that stoichiometric amount necessary to effect the lactonization. Preferably the water is present in at least a stoichiometric amount and up to about 2 times the stoichiometric amount, preferably 1 to 1.1 stoichiometric amount of water required for the lactonization.

Lactonization is facilitated through the use of a protonating agent or an electron pair acceptor. These agents act as a catalyst. Generally speaking, a concentrate of mineral acid can be employed, especially sulfuric acid. Other mineral acids particularly contemplated include perchloric acid. Organic acid can also be employed including p-toluene sulfonic acid hydrate. Electron acceptors such as boron trifluoride and boron trifluoride etherate are especially contemplated as well as solid acid catalysts such as sulfonic acid ion exchange resins including sulfonic acid macroreticular ion exchange resins.

The protonating agent or electron pair acceptor employed should provide from about 0.05 to 3, preferably 0.25 to 1.5 and most preferably 1.25 to 1.5 moles of protons or electron acceptors per mole of the alkenyl dicarboxylic acid anhydride being reacted although smaller or larger amounts can be employed with compromises in efficiency and/or economy. It is preferred to employ a protonating agent or electron pair acceptor which provides from about 0.5 to 1 moles of proton or electron pair per mole of alkenyl dicarboxylic acid anhydride.

The lactonization reaction is generally effected at a temperature ranging from about 25° C. up to about 200° C. with a range of from about 60° to 200° C. being especially contemplated with 90° to 100° C. representing a particularly preferred temperature range. The lactonization is effected for a period of time between one minute and five hours, preferably for a period of between one minute and up to one hour. The product is the lactone in unreacted polyolefin in admixture with the sludge and catalyst.

The product is thereafter passed over a filter to separate the sludge from the liquid components which can thereafter be extracted to remove water soluble components, chiefly catalyst. This is done using water with salt and cosolvents to break emulsions.

The product can be diluted with a non-polar solvent to change its viscosity, but such dilution step is not necessary. The dilution can be performed before or after the sludge is filtered off. When performed before, the dilution assists in the separation procedure by rendering the same more pourable. It has been found that the organic phase so separated contains remarkably less residual catalyst than present according to the multi-step process of the prior art.

In carrying out the essentially two-step, one-pot process of the invention, the lactonization is carried out in the presence of the aforenoted dark, solid granular mass sludge. Hydrolysis-lactonization is preferably effected after removal of the excess or unreacted unsaturated dicarboxylic acid anhydride. No benefit is observed in not removing the unreacted dicarboxylic anhydride, and, in fact, some deleterious effects to the overall process have been observed when unreacted dicarboxylic acid anhydride has been left in the reaction mixture during lactonization. Filtration of the resultant product is considerably more difficult in such instances and the final product is produced with a somewhat lower conversion.

It is particularly contemplated to react maleic acid, maleic acid anhydride, itaconic acid, itaconic acid anhydride, fumaric acid as well as other olefinically unsaturated dicarboxylic acids and anhydrides falling within the above description. These acids can be substituted by any one of the following groups: halogen, especially chloro and bromo, hydroxy, or aliphatic radicals, especially $C_{1-4}$ alkyl and $C_{2-4}$ alkenyl groups. Hence, acids such as citraconic and mesaconic are contemplated as well.

In carrying out the process, it is preferred to begin with the unsaturated dicarboxylic acid anhydride. If the acid is used, under the prevailing conditions, including high temperatures, the anhydride will be formed while water will be given off. However, the anhydride is unstable in the presence of the water and decomposition products can form. For this reason it is preferred to use the anhydride or, if using the acid, to additionally employ a dehydrating agent which will absorb the water chemically or physically as it is formed.

By carrying out the alkenyl dicarboxylic acid lactone preparation in accordance with the herein described procedure, not only are substantially fewer process steps invovled, but the resultant product is superior to products obtained by multi-stepped processes. For instance, when the process is carried out according to the described technique, characterized by the absence of a sludge removal step, employing sulfuric acid in the lactonization process, the resultant lactone product contains about 30% less sulfur than is obtained according to the multi-stepped process wherein the alkenyl dicarboxylic acid anhydride is isolated following the initial alkenylation procedure.

Products of the invention prepared through lactonization in the presence of a sulfur containing catalyst, especially sulfuric acid, are characterized by sulfur contents of less than 12.0 weight percent of the sulfur added compared to the combined amount of lactone and unreacted polyolefin after extraction of water soluble impurities.

In order to more fully illustrate the nature of the invention and the manner of practicing the same, the following examples are presented:

EXAMPLES

Example 1

A mixture containing 387.0 g (0.30 mole) of polyisobutene (average mole weight = 1290) and 58.8 g (0.60 mole) of maleic anhydride were stirred together and heated to 204° C. under a nitrogen sweep at atmospheric pressure for 16.5 hours. Then the pressure was reduced to 50 mm Hg at 204° C. with stirring while nitrogen was introduced below the surface of the reactor contents and distillation was conducted until the rate of distillate collected was negligible. The distillation residue was allowed to cool to about 95° C. and 3.60 g (0.20 mole) distilled water and 5.00 g (0.05 mole) of concentrated sulfuric acid were added. Stirring was continued for 1.0 hour.

From previous runs involving the alkenylation of maleic anhydride wherein the alkenylsuccinic anhydride intermediate was isolated and analyzed, it was determined, on the basis of the amount of water and acid catalyst added in lactonization, that about ⅔ of the polyisobutene involved in the alkenylation process had reacted. Accordingly, on this basis all the water was consumed in the hydrolysis of the anhydride and the lactone product contained virtually no water. The mole ratio of sulfuric acid to anhydride, assuming a ⅔ conversion of polyisobutene, was 0.125 : 1.

The reaction mixture was diluted with about 2 volumes of isooctane and filtered through a bed of filter aid. The filtered solution was extracted with water using salt and cosolvents to break emulsinos. The organic phase was separated and stripped to constant weight under a final condition of 80° C. and 2 mm Hg pressure.

Infrared spectroscopy showed both a strong 5- and a strong 6-membered ring lactone absorption in the range of 5.6 to 5.8 micrometers and a strong carboxylic acid absorption between 5.8 and 5.9 micrometers. There was no significant, relative absorption at 5.4 micrometers, indicating the alkenylsuccinic acid anhydride intermediate was no longer present.

The product had a saponification value of 46.25 indicating 58.0% conversion of the polyisobutene. Liquid chromatography on silica gel and infrared spectroscopy indicated that the product contained at least 57.6% and up to 62.2% of the desired acid lactone product.

The product had a neutralization number of 33.2 and a sulfur content of 0.041 percent. This corresponds to only 10.5 percent of the sulfur actually charged.

In this example the amount of $H_2SO_4$ employed assumed a ⅔ conversion into alkenylated product. The sulfur content can be still further reduced, therefore, if less $H_2SO_4$ is employed corresponding to the actual conversion of 58.0 percent.

Example 2

The process of Example 1 was repeated except that no distillation to remove unreacted maleic acid anhydride was performed. After alkenylation, the reaction mixture was allowed to cool to 95° C. whereupon hydrolysis-lactonization was initiated. Upon completion of the process, it was found that the reaction mass could be diluted, filtered and extracted only with greater difficulty than the product obtained in accordance with Example 1. The product had a saponification value of 38.9, indicating 49% conversion of the polyisobutene. The infrared spectrum indicated acid-lactonization was achieved in the presence of unreacted maleic anhydride. This modification is practical although less preferred than that wherein the unreacted or excess maleic acid anhydride is removed.

Example 3

A mixture of 335 g (1.0 mole) of Indopol L-14 polyisobutene (average mole weight 335) and 98 g (1.0 mole) of maleic anhydride were heated to 200° C. and stirred for 20 hours under autogenous pressure (est. 30 psig) after purging with nitrogen. The reactor was vented and allowed to cool to about 140° C. and the pressure was gradually reduced and the temperature increased to 210° C. to distill volatiles. The reactor was purged with nitrogen at atmospheric pressure and the reactor allowed to cool to 95° C. Eighteen grams (1.0 mole) of water and 25.0 grams (0.25 mole) of sulfuric acid were added assuming 100% conversion of the polyolefin in the alkenylation step. The mixture was stirred for 1 hour at 95° C. and was then diluted with isooctane and filtered. After stripping solvent, the product showed strong infrared absorptions indicative of 5- and 6-membered ring acid lactones.

Example 4

Alkenylsuccinic acid lactones were prepared on the same scale with the same reagents as specified above except that two successive processes were performed. The hydrolysis-lactonization catalyst was sulfuric acid containing 14 to 19% by weight sulfur. Alkenylsuccinic acid lactones prepared in accordance with Example 1 contained more than 30% less sulfur (introduced by sulfuric acid) than obtained when the alkenyl dicarboxylic acid anhydride intermediate was isolated from the sludge formed during the alkenylation. While not wishing to be bound by any theory, it is believed that the presence of the sludge from the alkenylation in the hydrolysis-lactonization step in effect absorbs a portion of the catalyst residues, thereby permitting a more effective extraction of the reaction products.

COMPARATIVE EXAMPLE

Example 5

Maleic acid anhydride was reacted with polyisobutene to form crude polyisobutenyl succinic anhydride (containing about 50% unreacted polyisobutene of about 1300 average molecular weight).

A mixture of 2,570 g (1.0 mole) of the crude polyisobutenyl succinic anhydride so obtained was reacted with 25 g (0.25 mole) of about 96% aqueous sulfuric acid and 18 g (1.0 mole) of water. The reaction mixture was heated and stirred at 90° C. for about one hour and then allowed to cool to room temperature.

The amount of sulfur charged was 0.306 weight percent of the reaction mixture. The amount of sulfur in the product was 0.26 weight percent.

The product was washed with a cosolvent mixture and the final sulfur content was determined to be 0.046 weight percent, corresponding to 15.0 weight percent of the sulfur initially charged. The product's saponification number was 43.6 and its average molecular weight was 1320.

In comparison, the procedure of Example 1 yields 30% less sulfur in fewer process steps.

COMPARATIVE EXAMPLE

Example 6

Known Preparation of Polyisobutenyl(335)Lactone Carboxylic Acid

To 369.0 g (0.5 mole active) of filtered polyisobutenyl (335) succinic acid, original via reaction of a polyisobutene with maleic acid anhydride, was added 9.0 ml (0.5 mole) of distill water and 12.5 g (0.125 mole) of sulfuric acid. This mixture was heated with stirring for 1½ hours at 100° C. The reaction mixture was analysed as follows:

Saponification Number: 163.4
Neutralization Number: 138.2
% S: 0.88

Example 7

Preparation of Polyisobutenyl (335) Lactone Carboxylic Acid According to the Invention To 738.0 g (1.0 mole active) of unfiltered polyisobutenyl (335) succinic acid, original via reaction of a polyisobutene with maleic acid anhydride was added 18.0 g (1.0 mole) of distilled water and 25.0 g (0.25 mole) of sulfuric acid. This mixture was heated with stirring at 100° C. for 1½ hours. The reaction mixture analysed as follows:

Saponification Number: 124.5
Neutralization Number: 144.2
% S: 0.63

What is claimed is:

1. A method for preparing an alkenyl-substituted acid lactone which comprises reacting maleic anhydride with an olefin having a molecular weight between 200 and 3000 under alkenylation conditions employing a temperature from 180° to 250° C. and a mole ratio of said maleic anhydride to olefin of from 1:2 to 3:1 to produce a reaction product comprising an alkenylsuccinic anhydride and a sludge, adding sulfuric acid and water to said reaction product to form a reaction mixture, said water being added in an amount between 1 and 2 times the stoichiometric amount of water required for hydrolysis of said anhydride to the corresponding acid, reacting said reaction mixture under lactonization conditions at a temperature in the range of 60° to 200° C. to form a second reaction product comprising an alkenyl-substituted acid lactone and a residue comprising said sludge and spent sulfuric acid catalyst, and recovering said alkenyl-substituted acid lactone from said second reaction product.

2. A process according to claim 1, wherein subsequent to said alkenylation and prior to said lactonization, unreacted unsaturated dicarboxylic acid anhydride is removed from the resultant reaction mixture.

3. A process according to claim 2, wherein the unreacted dicarboxylic acid anhydride is removed distillatively.

4. A process according to claim 1, wherein said lactonization is carried out employing between 1 and 1.1 times the stoichiometric amount of water required for said lactonization.

5. A process according to claim 1, wherein between 0.05 and 3 moles of sulfuric acid per mole of maleic anhydride are employed.

* * * * *